United States Patent [19]

Sugden

[11] Patent Number: 4,829,056
[45] Date of Patent: May 9, 1989

[54] BUCCAL TABLET COMPRISING ETORPHINE OR A SALT THEREOF

[75] Inventor: Keith Sugden, Beverley, Great Britain

[73] Assignee: Reckitt & Colman Products Limited, London, United Kingdom

[21] Appl. No.: 37,191

[22] Filed: Apr. 10, 1987

[30] Foreign Application Priority Data

Apr. 11, 1986 [GB] United Kingdom ................ 8608818

[51] Int. Cl.$^4$ .................. A61K 9/22; A61K 9/52; A61K 9/20; A61K 9/26

[52] U.S. Cl. ..................................... 514/54; 514/809; 514/974; 514/816; 514/817; 514/818; 514/948; 424/464; 424/465

[58] Field of Search ................ 514/54, 974, 816, 817, 514/818, 948, 809; 424/464, 465

[56] References Cited

U.S. PATENT DOCUMENTS

| | | | |
|---|---|---|---|
| 2,407,486 | 9/1946 | Flenner et al. | 514/223 |
| 3,218,232 | 11/1965 | Stein et al. | 514/223 |
| 4,076,804 | 2/1978 | Singiser | 514/29 |
| 4,126,684 | 11/1978 | Robson et al. | 514/282 |
| 4,244,944 | 1/1981 | Wilkinson | 514/809 |
| 4,244,945 | 1/1981 | Wilkinson | 514/809 |
| 4,315,936 | 2/1982 | Capetola et al. | 424/275 |
| 4,559,326 | 12/1985 | Crawford et al. | 514/224 |
| 4,598,087 | 7/1966 | Horwell | 514/471 |
| 4,599,342 | 7/1986 | LaHann | 514/282 |
| 4,673,679 | 6/1987 | Aungst et al. | 514/812 |

FOREIGN PATENT DOCUMENTS

| | | | |
|---|---|---|---|
| 0095944 | 6/1983 | European Pat. Off. | |
| 0107941 | 10/1983 | European Pat. Off. | |
| 0144243 | 12/1984 | European Pat. Off. | |
| 0205282 | 5/1986 | European Pat. Off. | |
| 2758942 | 12/1977 | Fed. Rep. of Germany | |
| 893228 | 6/1942 | France | |
| 981372 | 7/1961 | United Kingdom | |
| 1108376 | 10/1966 | United Kingdom | |
| 1531987 | 1/1976 | United Kingdom | |
| 1531987 | 11/1978 | United Kingdom | 424/80 |
| 2165451 | 10/1985 | United Kingdom | |
| 2165451A | 4/1986 | United Kingdom | |

OTHER PUBLICATIONS

Pharmacodynamics, vol. 68, 1986, p. 1890.

Primary Examiner—Ronald W. Griffin
Attorney, Agent, or Firm—Bacon & Thomas

[57] ABSTRACT

Pharmaceutical compositions in the form of a buccal tablet comprising etorphine or a salt thereof, at least one monosaccharide, disaccharide or a mixture thereof, and a mixture of xanthan gum and locust bean gum in a weight ratio 3:1 to 1:1, wherein the total weight of the mono- and/or di-saccharides relative to the combined weight of the xanthan and locust bean gums is in the ratio of 20:1 to 3:1. The tablet affords improved bioavailability.

10 Claims, No Drawings

BUCCAL TABLET COMPRISING ETORPHINE OR A SALT THEREOF

This invention relates to pharmaceutical compositions and in particular to compositions containing etorphine.

Etorphine (INN for 7,α-1-(S)-hydroxy-1-methylbutyl-6,14-endoetheno-6,7,8,14-tetrahydro-oripavine) in the form of the free base or its salts is a potent analgesic in both animals and man. Upon intramuscular administration to patients with a difficult pain control problem analgesia has been observed within 2-3 minutes of injection and has persisted for 1.5-2 hours. The majority of these patients were given etorphine in the dose range 50-400 ug which was judged to provide greater benefit relative to other analgesics. Studies in dog have shown etorphine to be more effective than morphine after sublingual administration. In patients sublingual etorphine was found to be beneficial with onset of effect occurring less than 10 minutes after tablet dissolution with the analgesic effect lasting for 1.5 to 4 hours.

Experiments in animals have shown that etorphine passes rapidly across the buccal mucosa and into the systemic circulation. We have now developed a buccal tablet that controls the release of the drug and thereby slows down the rate of absorption into the buccal tissue and thus increases the duration of analgesia.

According to this invention there is provided a buccal tablet comprising etorphine or a salt thereof, at least one monosaccharide, disaccharide or a mixture thereof, and a mixture of xanthan gum and locust bean gum in a weight ratio of 3:1 to 1:1, wherein the total weight of the mono-and/or di-saccharides relative to the combined weight of the xanthan and locust bean gums is in the ratio of 20:1 to 3:1 and preferably in the ratio of 12:1 to 5:1.

Suitable monosaccharides include glucose, galactose, fructose, mannose, mannitol and sorbitol. The disaccharides include maltose, lactose and sucrose, a preferred carrier being sucrose.

The tablets will normally contain 50 to 200 μg etorphine hydrochloride and conveniently 100 μg.

The locust bean gum is preferably a cold-water dispersible type such as Meyprodyn 200 (Registered Trade Mark, Meyhall Chemical A.G. Switzerland).

The tablets will preferably contain binding agents such as polyvinylpyrrolidone, lubricating agents such as magnesium stearate and/or glidants such as talc.

The tablets are prepared by standard tabletting procedures in which various components are blended together and the mixture directly compressed or else there is a pregranulation stage using for example a wet granulation with aqueous ethanol or isopropanol followed by the tabletting.

The buccal tablets of the present invention are placed between the gingival surface of the jaw and the buccal mucosa where they gel by water absorption to produce a soft hydrated tablet which may be retained in position giving prolonged and controlled release of the drug by diffusion for up to two hours.

The invention is illustrated by the following Examples:

EXAMPLES 1-3

Buccal tablets (60 mg) were prepared having the following compositions:

|  | mg |
|---|---|
| Xanthan Gum (Keltrol F) | x |
| Locust Bean Gum (Meyprodyn 200) | y |
| Etorphine HCl | 0.10 |
| Polyvinylpyrrolidone (Kollidon K30 BASF) | 1.20 |
| Sucrose (Microtal D.C.D. Tate and Lyle) | 57.20 − (x + y) |
| Talc | 1.0 |
| Magnesium Stearate | 0.50 |

| | where x and y are respectively: | | |
|---|---|---|---|
| Example | 1 | 2 | 3 |
| x = | 1.5 | 2.5 | 2.25 |
| y = | 1.5 | 2.5 | 0.75 |

The tablets were prepared by blending together the xanthan gum, locust bean gum, polyvinylpyrrolidone, and sucrose. The mixed powders were then wet granulated using an 8:5 (v/v) ethanol:water mixture, containing the dissolved etorphine HCl, by hand using a mortar and pestle. The damp granules were dried at 45° C. After drying the mass was passed through a 500 μm sieve, blended with the talc and magnesium stearate and compressed into 5.56 mm diameter normal concave tablets of nominal weight 60 mg and breaking strength 2-5 kp using a single punch tablet press.

EXAMPLES 4-6

Buccal tablets (60 mg) were prepared, having the composition of Examples 1-3, but also including the colouring agent erythrosine (6 μg) added to the 8:5 ethanol:water granulating fluid.

EXAMPLES 7-9

Buccal tablets (80 mg) were prepared having the composition:

|  | mg |
|---|---|
| Xanthan Gum (Keltrol F) | x |
| Locust Bean Gum (Meyprodyn 200) | y |
| Etorphine HCl | 0.10 |
| Polyvinylpyrrolidone (Kollidon 30 BASF) | 1.6 |
| Sucrose | 76.30 − (x + y) |
| Talc | 1.3 |
| Magnesium Stearate | 0.7 |

| | where x and y are respectively: | | |
|---|---|---|---|
| Example | 7 | 8 | 9 |
| x = | 5 | 6 | 7 |
| y = | 5 | 6 | 7 |

The granules bulk mixes were prepared as in Examples 1-3 and the tablets of nominal weight 80 mg and 6.35 mm normal concave profile were compressed on a single punch tablet press.

EXAMPLES 10-12

Buccal tablets (80 mg) were prepared, having the composition of Examples 7-9, but also including the colouring agent erythrosine (20 μg) added to the 8:5 ethanol:water granulating fluid.

EXAMPLES 13-15

Buccal tablets (80 mg) similar to those of Examples 7-9 were prepared using lactose B.P. in the place of the sucrose.

EXAMPLES 16-18

Buccal tablets (80 mg) similar to those of Examples 7-9 were prepared using mannitol in the place of the sucrose.

EXAMPLES 9-21

Buccal tablets (80 mg) similar to those of Examples 7-9 were prepared using anhydrous dextrose B.P. in the place of the sucrose.

EXAMPLES 22-24

Buccal tablets (80 mg) similar to those of Examples 7-9 were prepared using fructose in the place of the sucrose.

EXAMPLES 25-27

Buccal Tablets (80 mg) similar to those of Examples 7-9 were prepared using sorbitol in the place of the sucrose.

The in-vitro release rate of the buccal tablets was investigated using a method based on British Pharmacopoeia 1980, Volume II, A114. Tablets were placed in a standard wire gauze basket (Copley Instruments (Nottingham) Limited) and rotated at 100 rpm in 100 ml of 0.1M phosphate buffer (pH 6.7) contained in a 150 ml tall form beaker, placed in a water bath maintained at $37\pm1°$ C. At intervals 200 μl aliquots were removed and replaced by 200 μl buffer. The sample solutions (50 μl) were assayed for etorphine content by high performance liquid chromatography using 1% aqueous ammonium acetate:methanol (40:60) as the mobile phase delivered at 2 ml/min (by a Kontron 420 pump) through a 10 cm×0.46 cm id stainless steel column packed with Hypersil 5 μm ODS packing material. Etorphine content was monitored by electrochemical detection using a BAS LC4-B detector at a potential of +0.75 volts (0.5 nA f.s.d.). Quantitation was carried out automatically using a Hewlett-Packard 3390 or 3393 computing integrator.

The Table presents data of in-vitro dissolution of Examples 1 and 2.

TABLE

| Time | % released | |
|---|---|---|
| Hours | Example 1 | Example 2 |
| 0 | 0 | 0 |
| 0.5 | 41.2 | 24.3 |
| 1 | 76.3 | 57.2 |
| 2 | 97.1 | 71.9 |
| 3 | — | 83.4 |

From the results it can be seen that the rate of drug release decreases with increasing xanthan and locust bean gum content.

Tables containing xanthan/Meyprodyn gum mixtures gel in the mouth by water absorption to give a soft tablet which adheres to the buccal mucosa and subsequently remains in position for up to two hours.

Comparative tablets containing none of the gum mixture do not gel, but tend to remain in position as the tablet wets, however when fully hydrated the tablet disintegrates to hard course particles that have no adhesive properties. Such tablets have undesirable organoleptic properties and their inherent inability to adhere to the mucosa makes them less likely to give satisfactory buccal absorption and makes them less acceptable than the soft buccal tablets of this invention.

We claim:

1. A buccal tablet comprising etorphine or a salt thereof, at least one monosaccharide, disaccharide or a mixture thereof, and a mixture of xanthan gum and locust bean gum in a weight ratio 3:1 to 1:1, wherein the total weight of the mono- and/or di-saccharides relative to the combined weight of the xanthan and locust bean gums is in the ratio of 20:1 to 3:1.

2. A buccal tablet as claimed in claim 1 wherein the total weight of the mono- and/or di-saccharides relative to the combined weight of the xanthan and locust bean gums is in the ratio of 12:1 to 5:1.

3. A buccal tablet as claimed in claim 1 wherein the weight of etorphine is between 50 and 200 μg.

4. A buccal tablet as claimed in claim 1, wherein the monosaccharide is glucose, galactose, fructose, mannose, mannitol or sorbitol.

5. A buccal tablet as claimed in claim 1, wherein the disaccharide is maltose, lactose or sucrose.

6. A buccal tablet as claimed in claim 2, wherein the weight of etorphine is between 50 and 200 μg.

7. A buccal tablet as claimed in claim 2, wherein the monosaccharide is glucose, galactose, fructose, mannose, mannitol or sorbitol.

8. A buccal tablet as claimed in claim 3, wherein the monosaccharide is glucose, galactose, fructose, mannose, mannitol or sorbitol.

9. A buccal tablet as claimed in claim 2, wherein the disaccharide is maltose, lactose or sucrose.

10. A buccal tablet as claimed in claim 3, wherein the disaccharide is maltose, lactose or sucrose.

* * * * *